(12) United States Patent
Sievers et al.

(10) Patent No.: US 10,507,100 B2
(45) Date of Patent: Dec. 17, 2019

(54) HEART VALVE PROSTHESIS

(71) Applicant: Hans-Hinrich Sievers, Kronshagen (DE)

(72) Inventors: Hans-Hinrich Sievers, Kronshagen (DE); Michael Scharfschwerdt, Lübeck (DE); Andreas Hof, Lübeck (DE)

(73) Assignee: Hans-Hinrich Sievers, Kronshagen (DE)

( * ) Notice: Subject to any disclaimer, the term of this patent is extended or adjusted under 35 U.S.C. 154(b) by 0 days.

(21) Appl. No.: 15/562,142

(22) PCT Filed: Mar. 23, 2016

(86) PCT No.: PCT/DE2016/200152
§ 371 (c)(1),
(2) Date: Sep. 27, 2017

(87) PCT Pub. No.: WO2016/155731
PCT Pub. Date: Oct. 6, 2016

(65) Prior Publication Data
US 2018/0078364 A1    Mar. 22, 2018

(30) Foreign Application Priority Data

Apr. 2, 2015    (DE) .................. 10 2015 206 097

(51) Int. Cl.
*A61F 2/24*    (2006.01)

(52) U.S. Cl.
CPC .......... *A61F 2/2409* (2013.01); *A61F 2/2412* (2013.01); *A61F 2220/0008* (2013.01)

(58) Field of Classification Search
None
See application file for complete search history.

(56) References Cited

U.S. PATENT DOCUMENTS

| | | | |
|---|---|---|---|
| 5,855,602 A * | 1/1999 | Angell | A61F 2/2409 606/1 |
| 6,951,573 B1 | 10/2005 | Dilling | |
| 2004/0176839 A1 | 9/2004 | Huynh et al. | |
| 2007/0005134 A1 | 1/2007 | McCarthy | |
| 2012/0059458 A1 | 3/2012 | Buchbinder et al. | |
| 2014/0039613 A1 | 2/2014 | Navia et al. | |

FOREIGN PATENT DOCUMENTS

DE    10 2010 051 632 B4    9/2013

* cited by examiner

*Primary Examiner* — Leslie Lopez
(74) *Attorney, Agent, or Firm* — McGlew and Tuttle, P.C.

(57) ABSTRACT

A heart valve prosthesis includes a downstream first axial end (6) and an upstream second axial end (8) and a stitching ring (10) extending in an arcuate manner for stitching in a blood vessel. The arcuate course of the stitching ring (10) is formed by three arcs (12) and three transition regions (14). At each end of two of the arcs (12) transition into each other. The stitching ring (10) has a movable tab (18) at at least one of the three transition regions (14). The movable tab (18) can be selectively directed toward the first axial end (6) or folded over toward the second axial end (8).

6 Claims, 1 Drawing Sheet

HEART VALVE PROSTHESIS

CROSS REFERENCE TO RELATED APPLICATIONS

This application is a United States National Phase Application of International Application PCT/DE2016/200152, filed Mar. 23, 2016, and claims the benefit of priority under 35 U.S.C. § 119 of German Application 10 2015 206 097.7, filed Apr. 2, 2015, the entire contents of which are incorporated herein by reference.

FIELD OF THE INVENTION

The invention relates to heart valve prosthesis with a sewing ring for sewing in a blood vessel.

BACKGROUND OF THE INVENTION

Heart valve prostheses, in particular biological heart valve prostheses which comprise a sewing ring which runs in an arched manner (scalloped sewing ring) and along which the heart valve prosthesis can be sewn to the blood vessel are known. Here, it is a problem that the arched or scalloped course of the sewing ring does not match all anatomies, so in individual cases the sewing becomes difficult or is only possible with an undesired deformation of the blood vessel or of the heart valve prosthesis.

SUMMARY OF THE INVENTION

With regard to this problem, it is an object of the invention to improve a heart valve prosthesis to the extent that it can be sewn into a blood vessel without any problem, given a multitude of different anatomies and in particular given asymmetrically shaped aortic valves.

The heart valve prosthesis according to the invention in particular is a heart valve prosthesis for the replacement of the aortic valve. The heart valve prosthesis according to the invention, considered in the envisaged flow direction of the blood, comprises a first downstream axial end and a second axial end which is situated upstream. Moreover, the heart valve prosthesis comprises a sewing ring (suture ring) which serves for sewing the heart valve prosthesis into a blood vessel. This sewing ring is preferably situated in the region of the second axial end or situated closer to the second axial end than to the first axial end. The sewing ring has an arched (arcuate) course which is composed of three arches which with their ends abut one another or merge into one another. Transition regions which have an essentially V-shaped shape are formed where the arches abut one another or merge into one another, wherein this V-shaped shape is open to the second axial end, whilst the arches are open to the first axial end.

The sewing ring moreover comprises a movable tab on at least one of the transition regions which are formed in such a manner. This movable tab has a greater free length than the remaining regions of the sewing ring. The tab is configured such that it can be selectively directed towards the first axial end or can be folded over towards the second axial end. This means that the tab comprises a base or base edge which is connected to the sewing ring and from which it extends away to the free end, wherein this free end can either be directed to the first axial end or to the second axial end, depending on the direction, in which the tab is folded. The ability of the tab to be folded over permits the part of the sewing ring which is formed by the tab to be directed or positioned as is demanded by the anatomy of the patient. A greater flexibility of the sewing is therefore rendered possible since the seam does not necessary need to follow the arched course of the sewing ring, but where the tab is arranged, the necessary stitches can also be placed at a different position by way of a suitable folding or aligning of the tab.

Preferably, such a movable tab which can be selectively directed to the first axial end or folded over towards the second axial end is arranged or formed on two or each of the three transition regions. The flexibility of permitting the seam to either follow the arched course of the sewing ring or however also of being able to sew the heart valve prosthesis to the blood vessel in a manner differing from this course when the tab is directed which is to say folded over accordingly therefore preferably exists in each of the transition regions.

The sewing ring is preferably configured such that when the tab or the tabs are directed towards the first axial end, the sewing ring is configured in a strip-like manner (strip/strip shape) and has an essentially constant width along its arched course. This means that the sewing ring is configured such that when it is directed or folded towards the first axial end, the tab defines a shape which corresponds to the known arched course of the sewing ring. Here, the tab preferably comes to lie on the parts of the sewing ring which lie therebelow which is to say covers a part of the sewing ring which lies further radially inwards. When it is directed towards the first axial end, the tab preferably defines the tip of the transition region between two arches of the sewing ring. A course of the seam can therefore be realized with the known contour which is defined by the arched sewing ring.

At its side or side edge which faces the second axial end, the sewing ring preferably comprises an arched contour which is formed from three arches. This means that when the tab is folded towards the first axial end, the sewing ring towards the second seam end defines the described arcuate shape composed of three arches, wherein free spaces or the free spandrels which are not covered by the sewing ring are formed below the transition regions, which is to say between the transition regions and the second axial end, between the arches which are adjacent one another. An arched shape of the sewing ring is therefore achieved and this shape corresponds to the arcuate course of the edges of a normally formed, natural aortic valve and can therefore be optimally admitted into the common anatomy of the blood vessel in the region of the aortic valve.

The tab or the tabs is/are further preferably each configured such that when they are directed towards the second axial end, which is to say folded over, they at least partly cover an indentation of the sewing ring which is formed by two arches which are adjacent one another. This indentation is the free space which is formed by the V-shaped shape of the transition region which is open to the second axial end. This is the free spandrel between the adjacent arches which is mentioned above. Due to the fact that this spandrel can be at least partly covered by the tab, a sewing selectively in the arched course is also rendered possible in this region, in order to permit an adaptation to different anatomies, in particular to asymmetrical anatomies.

Particularly preferably, the tab or the tabs are shaped in a manner such that when they are folded over towards the second axial end, they extend in the axial direction towards this second axial end at least up to a peripheral line which runs through the apex points of the arches of the sewing ring, said apex points facing the second axial end. This means that when the tabs are directed or folded over towards the second axial end, the tips of the tabs extend in the axial direction towards the second axial end essentially just as far as the arches. This permits an essentially annular course of the seam when the tabs are aligned in this manner.

Particularly preferably, the sewing ring is hence configured in a manner such that an essentially annulus-shaped or circle-segment-shaped sewing (seam) region, along which the heart valve prosthesis can be sewn to a blood vessel is defined when the tabs are directed toward the second axial end which is to say folded over. The annulus-shaped sewing region here extends over the tab or tabs and over the sections of the arches which are adjacent to the apex points. It is to be understood that inasmuch as three tabs are provided, all three tabs can be aligned in this manner, depending on the anatomy. However, it is alternatively also possible for example to fold over only one tab towards the second axial end and in the two other transition regions to leave two other tabs in their position directed towards the first axial end.

Further preferably, the sewing ring is configured in a manner such that when the tabs are directed towards the first axial end, the sewing ring defines an arcuate sewing region which runs in a manner such that it permits a sewing in the aorta along the normal course of the edge of the natural valve leaflet of the aortic valve. The heart valve prosthesis can thus be sewn with seam (stitch) course which follows the common anatomy of the natural aortic valves. In the case of an anatomy which differs from this normal anatomy, for example if only two natural valve leaflets were present, possibly at least one tab is folded over towards the second axial end in the manner described above. For this reason, the sewing ring comprises a tab as has been hitherto described, preferably at least at one transition region.

Further preferably, the sewing ring is configured in a manner such when they are directed towards the first axial end, the tabs define the axial end regions of the sewing ring which face the first axial end. If only one tab is provided, then the axial end region of the sewing ring is defined by the tab only in that transition region, at which the tab is arranged. A continuous course of the sewing ring without such tabs is then envisaged in the two other transition regions. If such tabs are provided in all transition regions, then the tabs in all transition regions define the axial end region of the sewing ring which faces the first axial end. If the tab or tabs are folded over towards the second axial end, then the end region of the sewing ring which faces the first axial end is either defined by the side edge of the tab, about which side edge the tab is folded, or by a region of the sewing ring which lies below the tab which is to say which lies further radially inwards.

The heart valve prosthesis is preferably configured as a semilunar valve with three valve leaflets, particularly preferably with three valve leaflets of biological material, wherein the arches of the sewing ring extend essentially parallel to the fastening edge of the valve leaflets which faces the second axial end. The valve leaflets are usually fastened to arched sections of a valve frame, and the arches of the sewing ring extend parallel to the arches of this valve frame.

The transition regions of the sewing ring, in which the tabs are arranged preferably lie at the peripheral positions of the heart valve prosthesis, at which positions the commissures of the heart valve prosthesis are situated. An optimal adaptation to the natural anatomy is therefore possible.

Preferably, the tabs each have an essentially triangular shape and can be folded over along a side edge which runs in the peripheral direction of the heart valve prosthesis, to the second axial end. This side edge, about which the tab can be folded over, is preferably the longest side edge of the tab. The side edge thereby runs arcuately in the peripheral direction.

The invention is hereinafter described by way of example and by way of the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
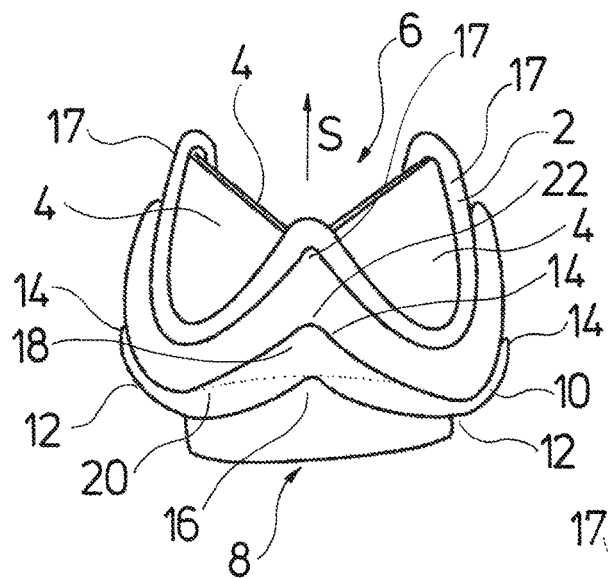
FIG. 1 is a schematic perspective view of a heart valve prosthesis according to the invention, with the sewing ring in a first condition.

Referring to the drawings, The heart valve prosthesis according to the invention and which is shown in FIG. 1 comprises a valve frame 2, to which three valve leaflets 4 of biological material are fastened. The valve leaflets 4 abut one another in the known manner at the first axial end 6 which is upstream in the flow direction S. A fastening region, in which a sewing ring 10 is situated, is formed at the opposite, upstream second axial end 8. The sewing ring 10 in the known manner is configured from a material which can be pierced, in particular from a fabric material and serves for sewing the heart valve prosthesis to the tissue of a blood vessel. The represented sewing ring 10 in the initial condition which is represented in FIG. 1 is configured in an arched manner, wherein it is formed by three arches 12, of which two arches 12 always abut one another or merge into one another in a transition region 14. The transition region 14 comprises a tip which is directed towards the first axial end 6, and is open towards the second axial end 8 in a V-shaped manner, so that a free space 16 or free spandrel 16 remains between the adjacent arches 12 in a manner facing the second axial end 8. The free space 16 thus forms an indentation into the sewing ring 10, said indentation departing from the second axial end 8. The arched course of the sewing ring which is thus created is configured such that the transition regions 14 lie in the region of the commissures 17 of the heart valve prosthesis and the arches 12 extend parallel to the arches of the valve frame 2, on which latter mentioned arches the valve leaflets 4 are fastened. A course of the sewing ring 10 which corresponds essentially to the natural course of the edge of the valve leaflets of a normal aortic valve is therefore created in this manner. The sewing ring can be used in this form for the replacement of a normally formed aortic valve since the heart valve prosthesis can be sewn to the edge of the natural valve leaflet in this manner.

In the condition shown in FIG. 1, the sewing ring 10 over its course has an essentially constant width, wherein in particular the side edge of the sewing ring 10 which faces the second axial end 8 has the described arched course. In this condition, the free ends 22 of the tabs 18 form the tips or ends of the sewing ring 10 which face the first axial end 6.

However, in order to be able to use the aortic valve prosthesis which is shown here, also with differing, in particularly asymmetrical anatomies, the sewing ring 10 in the transition regions 14 comprise tabs 18 which are freely movable. In this embodiment, a tab 18 is only represented in one transition region 14. However, it is to be understood that the two other transition regions 14 can also be configured in the same manner. The tab 18 is essentially triangular and is connected along its longest side edge 20 which extends in the peripheral direction, to the sewing ring 10. The tab 18 is freely movable in a manner such that it can be folded in two positions, wherein a first position is shown in FIG. 1 and the second position in FIGS. 2 and 3. In the position shown in FIG. 1, the tab 18 with its tip, which is to say with its free end 22, is folded towards the first axial end 6. In this position, the tab 18 lies completely in the arcuate course of the sewing ring 10, so that an accordingly arched stitching region is created and the free space 16 remains free as an indentation.

Figure 2:
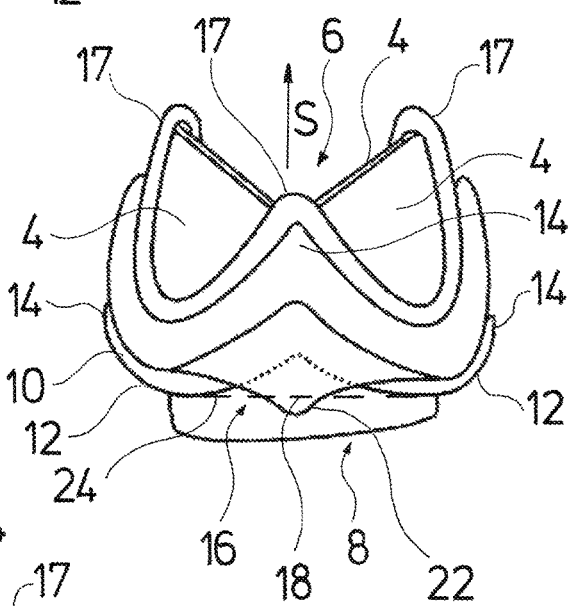
FIG. 2 is a schematic perspective view of a heart valve prosthesis according to the invention, with the sewing ring in a second condition.
Figure 3:
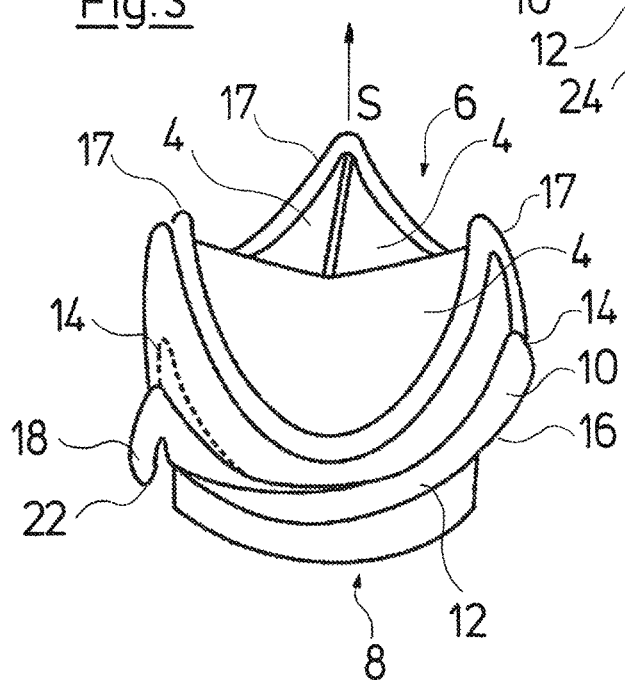
FIG. 3 is a lateral view of the heart valve prosthesis which has been rotated by 90° compared to FIG. 2, in the condition represented in FIG. 2.

In the second position which is represented in FIGS. 2 and 3, the tab 18 is folded over with its free end 22 towards the second axial end 8, wherein the tab 18 is folded about its long side edge 20 which runs in the peripheral direction. The tab 18 with its free end thus projects into the free space 16 and covers this. The free end 22 of the tab 18 here extends beyond a peripheral line 24 which runs through or over the apex points of the arches 12. This means that the free end 22 extends in the axial direction extends to the second axial end 8 just as far or further than the arches 12. Since the free space 16 is covered at least to a significant extent by way of this, it is possible to select an annular or arc-shaped stitching course which runs parallel to the peripheral line 24. This means that the heart valve prosthesis does not need to be sewn along the otherwise usual arched course in the transition region 14. A simple sewing-in is hence also possible in the case of asymmetrical anatomies, without having to deform the blood vessel or the heart valve prosthesis.

While specific embodiments of the invention have been shown and described in detail to illustrate the application of the principles of the invention, it will be understood that the invention may be embodied otherwise without departing from such principles.

The invention claimed is:

1. A heart valve prosthesis comprising:
   a downstream first axial end;
   an upstream second axial end;
   a sewing ring extending in an arched course for sewing in a blood vessel, the arched course of the sewing ring being formed by three arches and three transition regions, wherein a respective transition region is arranged between an arch end of one of the arches and an arch end of another one of the arches, wherein the sewing ring further comprises a plurality of tabs, each of the tabs being associated with one of the three transition regions, each of the tabs comprising a folded state and a non-folded state, each of the tabs comprising a tab end, the tab end of each of the tabs facing the first axial end in the non-folded state, the tab end of each of the tabs facing the second axial end in the folded state, the tabs being located radially beyond the sewing ring in the folded state with respect to a longitudinal axis of the sewing ring.

2. The heart valve prosthesis according to claim 1, wherein the tabs extend in an axial direction towards the second axial end at least up to a peripheral line which extends through vertex points of the arches of the sewing ring, the vertex points facing the second axial end.

3. The heart valve prosthesis according to claim 2, wherein each vertex point is located radially beyond the sewing ring with respect to the longitudinal axis of the sewing ring.

4. A heart valve prosthesis comprising:
   a downstream first axial end;
   an upstream second axial end;
   a sewing ring comprising three arches and three transition regions, the three arches and the three transition regions defining an arched course for sewing in a blood vessel, wherein a respective transition region is arranged between an arch end of one of the arches and an arch end of another one of the arches, the sewing ring further comprising a plurality of tabs, each of the tabs being associated with one of the three transition regions, each of the tabs comprising a folded state and a non-folded state, each of the tabs comprising a tab end, the tab end of each of the tabs facing the first axial end in the non-folded state, the sewing ring comprising a sewing ring end portion at the second axial end, the tab end of each of the tabs facing the second axial end in the folded state, the tab end of each of the tabs being located at a first distance from the sewing ring end portion in the folded state, each of the arches comprising a lowermost point, the lowermost point of each of the arches being located at a second distance from the sewing ring end portion, the second distance being greater than the first distance.

5. The heart valve prosthesis according to claim 4, wherein the tabs extend in an axial direction towards the second axial end at least up to a peripheral line which extends through each lowermost point of the arches of the sewing ring, each lowermost point facing the second axial end, the peripheral line being located at an axial distance from the sewing ring end portion, the first distance being less than the axial distance.

6. The heart valve prosthesis according to claim 4, wherein each lowermost point is located radially beyond the sewing ring with respect to a longitudinal axis of the sewing ring.

* * * * *